United States Patent [19]

Bryan et al.

[11] Patent Number: 5,707,848
[45] Date of Patent: Jan. 13, 1998

[54] CALCIUM FREE SUBTILISIN MUTANTS

[75] Inventors: Philip N. Bryan; Patrick A. Alexander, both of Silver Spring; Susan L. Strausberg, Rockville, all of Md.

[73] Assignee: University of Maryland, College Park, Md.

[21] Appl. No.: 562,833

[22] Filed: Nov. 27, 1995

Related U.S. Application Data

[62] Division of Ser. No. 69,863, Jun. 1, 1993, Pat. No. 5,470,733.

[51] Int. Cl.$^6$ ............... C12N 15/57; C12N 15/75; C12N 15/63; C12N 9/54
[52] U.S. Cl. ............. 435/222; 435/69.1; 435/172.3; 435/221; 435/252.3; 435/252.31; 435/320.1; 536/23.2; 935/14; 935/29; 935/72; 935/75
[58] Field of Search ................ 435/220, 221, 435/222, 69.1, 172.3, 252.3, 252.31, 320.1; 536/232

[56] References Cited

U.S. PATENT DOCUMENTS

| | | | |
|---|---|---|---|
| 4,914,031 | 4/1990 | Zukowski et al. | 435/222 |
| 4,990,452 | 2/1991 | Bryan et al. | 435/222 |
| 5,013,657 | 5/1991 | Bryan et al. | 435/172.3 |
| 5,185,258 | 2/1993 | Caldwell et al. | 435/220 |
| 5,470,733 | 11/1995 | Bryan et al. | 435/222 |
| 5,567,601 | 10/1996 | Bryan et al. | 435/222 |

OTHER PUBLICATIONS

Abrahmsén et al, "Engineering Subtilisin and Its Substrates for Efficient Ligation of Peptide Bonds in Aqueous Solution," *Biochemistry*, 30(17):4151–4159 (1991).
Betzel et al, "Crystal Structure of the Alkaline Proteinase Savinase™ from *Bacillus lentus* at 1·4 Å Resolution," *J. Mol. Biol.*, 223:427–445 (1992).
Betzel et al, "Thermitase and Proteinase K: A Comparison of the Refined Three Dimensional Structures of the Native Enzymes," *Protein Engineering*, 3(3)161–172 (1990).
Braxton et al, "Incorporation of a Stabilizing Ca$^{2+}$–Binding Loop into Subtilisin BPN'," *Biochemistry*, 31:7796–7801 (1992).
Bryan et al, "Energetics of Folding Subtilisin BPN'," *Biochemistry*, 31(21):4937–4945 (1992).
Bryan et al, "Biotechnology Research and Applications", Gavora, J., et al., Eds., Elsevier Publishing Co., 57–67 (1988).
Bryan et al, "Site-Directed Mutagenesis and the Role of The Oxyanion Hole in Subtilisin," *Proc. Natl. Acad. Sci. USA*, 83:3743–3745 (1986).
Bryan, "Engineering Dramatic Increases in the Stability of Subtilisin," in *Pharmaceutical Biotechnology*, vol. Part B, Plenum Press, New York, 147–181 (1992).
Bryan et al, "Proteases of Enhanced Stability: Characterization of a Thermostable Variant of Subtilisin," *Proteins: Structure, Function, and Genetics*, 1:326–334 (1986).

Bryant, "Quin 2: The Dissociation Constants of its Ca$^{2+}$ and Mg$^{2+}$ Complexes and its Use in a Fluorimetric Method for Determining the Dissociation of CA$^{2+}$–Protein Complexes," *Biochemistry J.*, 226:613–616 (1985).
Carrara et al, *Archives of Biochemistry and Biophysics*, 294(1):107–114 (1992).
Chen et al, "Low–Temperature Unfolding of a Mutant of Phage T4 Lysozyme. 2. Kinetic Investigations," *Biochemistry*, 28:691–699 (1989).
Cunningham et al, "Improvement in the Alkaline Stability of Subtilisin Using an Efficient Random Mutagenesis and Screening Procedure," *Protein Engineering*, 1(4):319–325 (1987).
Deleage et al, *Analytical Biochemistry*, 163:292–297 (1987).
Eder et al, *Biochemistry*, 32(1):18–26 (1993).
Fahnestock et al, "Protease–Deficient *Bacillus subtilis* Host Strains for Production of Staphylococcal Protein A," *Appl. Environ. Microbiol*, 53(2):379–384 (1987).
Finzel et al, "The 1.2A Crystal Structure of a Subtilisin BPN'," *J. Cell. Biochem.*, Suppl. 10A:272 (1986).
Frömmel et al, *Proteins: Structure, Function, and Genetics*, 5(1):22–37 (1989).
Gallagher et al, "Calcium–Independent Subtilisin by Design," *Proteins: Str. Funct. Gen.*, vol. 16, 1993, pp. 205–213 (1993).
Gros, et al, "Calcium Binding To Thermitase," *J. Biol. Chem.*, 266(5):2953–2961 (1991).
Heiner et al, *Proteins; Structure, Function, and Genetics*, 14:451–464 (1992).
Holmes et al, "Structure of Thermolysin Refined at 1·6 Å Resolution," *J. Mol. Biol.*, 160:623–639 (1982).
Jacobs et al, "Cloning, Sequencing and Expression of Subtilisin Carlsberg From *Bacillus licheniformis*," *Nucleic Acids Research*, 13(24):8913–8926 (1985).
Jany et al, "Amino Acid Sequence of Proteinase K From the Mold *Tritirachium album* Limber," *FEBS Letters*, 199(2):139–144 (1986).
Kurihara et al, "Subtilisin Amylosacchariticus III. Isolation and Sequence of the Chymotryptic Peptides and the Complete Amino Acid Sequence," *J. Biol. Chem.*, 247(17):5619–5631 (1972).
Livingstone et al, "Contribution to the Thermodynamics of Protein Folding from the Reduction in Water–Accessible Nonpolar Surface Area," *Biochemistry*, 30:4237–4244 (1991).
McPhalen et al, "Crystal and Molecular Structure of the Serine Proteinase Inhibitor CI–2 from Barley Seeds," *Biochemistry*, 26(1):261–269 (1987).

(List continued on next page.)

*Primary Examiner*—Robert A. Wax
*Assistant Examiner*—William W. Moore
*Attorney, Agent, or Firm*—Burns, Doane, Swecker, & Mathis, L.L.P.

[57] ABSTRACT

Novel calcium free subtilisin mutants are taught, in particular a subtilisin which has been mutated to eliminate amino acids 75–83.

27 Claims, 6 Drawing Sheets

OTHER PUBLICATIONS

McPhalen et al, "Structure Comparison of Two Serine Proteinase–Protein Inhibitor Complexes: Eglin–C–Subtilisin Carlsberg and CI-2 Subtilisin Novo," *Biochemistry*, 27(17):6582–6598 (1988).

Meloun et al, "Complete Primary Structure of Thermitase from *Thermoactinomyces vulgaris* and its Structural Features Related to the Subtilisin–type Proteinases," *FEBS LETTERS*, 183(2):195–200 (1985).

Narhi et al, *Biotechnology and Applied Biochemistry*, 13(1):12–24 (1991).

Nedkov et al, "Determination of the Complete Amino–Acid Sequence of Subtilisin DY and its Comparison with the Primary Structures of the Subtilisins BPN', Carlsberg and Amylosacchariticus," *Biol. Chem. Hoppe–Seyler*, 366:421–430 (1985).

Pantoliano et al, "Protein Engineering of Subtilisin BPN': Enhanced Stabilization through the Introduction of Two Cysteines To Form a Disulfide Bond," *Biochemistry*, 26(8):2077–2082 (1987).

Pantoliano et al, "Large Increases in General Stability for Subtilisin BPN' Through Incremental Changes in the Free Energy of Unfolding," *Biochemistry*, 28(18):7205–7213 (1989).

Pantoliano et al, "The Engineering of Binding Affinity at Metal Ion Binding Sites for the Stabilization of Proteins: Subtilisin as a Test Case," *Biochemistry*, 27(22):8311–8317 (1988).

Privalov et al, "Stability of Protein Structure and Hydrophobic Interaction," *Adv. Protein Chem.*, 39:191–234 (1988).

Privalov et al, "Scanning Microcalorimetry in Studying Temperature–Induced Changes in Proteins," *Meth.Enzym.*, 131:4–51 (1986).

Rollence et al, "Engineering Thermostability in Subtilisin BPN' by *in vitro* Mutagenesis," *CRC Critical Rev. Biotechnol.*, 8(3):217–224 (1988).

Siezen et al, "Homology modelling and protein engineering strategy of subtilases, the family of subtilisin–like serine proteinases," *Protein Engineering*, 4(7):719–737 (1991).

Strausberg et al, *Biochemistry*, 32(32):8112–8119 (1993).

Svendsen et al, "Complete Amino Acid Sequence of Alkaline Mesenteriocopeptidase. A Subtilisin Isolated from a Strain of *Bacillus mesentericus*," *FEBS LETTERS*, 196(2):228–232 (1986).

Vasantha et al, "Genes for Alkaline Protease and Neutral Protease from *Bacillus amyloliquefaciens* Contain a Large Open Reading Frame Between the Regions Coding for Signal Sequence and Mature Protein," *J. Bacteriol.*, 159(3):811–819 (1984).

Vita et al, *Protein Engineering*, 1(3):265 (1987).

Voordouw et al, "Role of Bound Calcium Ions in Thermostable, Proteolytic Enzymes. Separation of Intrinsic and Calcium Ion Contributions on the Kinetic Thermal Stability," *Biochemistry*, 15(17):3716–3724 (1976).

Wells et al, "Subtilisin—an enzyme designed to be engineered," *TIBS*, 13:291–297 (1988).

Wells et al, "Cloning, sequencing, and secretion of *Bacillus amyloliquefaciens* subtilisin in *Bacillus subtilis*," *Nucleic Acids Res.*, 11(22):7911–7925 (1983).

Wiseman et al, "Rapid Measurement of Binding Constants and Heats of Binding Using a New Titration Calorimeter," *Analytical Biochemistry*, 179–131–137 (1989).

Zoller et al, "Oligonucleotide–directed Mutagenesis of DNA Fragments Cloned Into M13 Derived Vectors," *Meth. Enzym.*, 100:468–500 (1983).

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 1868 base pairs
        ( B ) TYPE: nucleic acid
        ( C ) STRANDEDNESS: single
        ( D ) TOPOLOGY: linear     ( i i ) MOLECULE TYPE: DNA (genomic)

( i x ) FEATURE:
        ( A ) NAME/KEY: CDS
        ( B ) LOCATION: 450..1599

( i x ) FEATURE:
        ( A ) NAME/KEY: mat_peptide
        ( B ) LOCATION: 772..1599

( i x ) FEATURE:
        ( A ) NAME/KEY: misc_feature
        ( B ) LOCATION: 450
        ( D ) OTHER INFORMATION: /note= "Amino Acid Val at position 450 is fMet."

( x i ) SEQUENCE DESCRIPTION: SEQ ID NO:1:

```
TTTTTCCGCA  ATTATATCAT  TGACAATATC  AACATCAATG  ATATTCATTA  TCATTATTTT      60

TATAAAATGG  TTTCACAGCT  TTTCTCGGTC  AAGAAAGCCA  AAGACTGATT  TCGCTTACGT     120

TTCCATCAGT  CTTCTGTATT  CAACAAAAGA  TGACATTTAT  CCTGTTTTTG  GAACAACCCC     180

CAAAAATGGA  AACAAACCGT  TCGACCCAGG  AAACAAGCGA  GTGATTGCTC  CTGTGTACAT     240

TTACTCATGT  CCATCCATCG  GTTTTTTCCA  TTAAAATTTA  AATATTTCGA  GTTCCTACGA     300
```

```
AACGAAAGAG AGATGATATA CCTAAATAGA AATAAAACAA TCTGAAAAAA ATTGGGTCTA        360

CTAAAATATT ATTCCATACT ATACAATTAA TACACAGAAT AATCTGTCTA TTGGTTATTC        420

TGCAAATGAA AAAAAGGAGA GGATAAAGA GTG AGA GGC AAA AAA GTA TGG ATC         473
                                Val Arg Gly Lys Lys Val Trp Ile
                                -107     -105              -100

AGT TTG CTG TTT GCT TTA GCG TTA ATC TTT ACG ATG GCG TTC GGC AGC         521
Ser Leu Leu Phe Ala Leu Ala Leu Ile Phe Thr Met Ala Phe Gly Ser
            -95              -90                  -85

ACA TCC TCT GCC CAG GCG GCA GGG AAA TCA AAC GGG GAA AAG AAA TAT         569
Thr Ser Ser Ala Gln Ala Ala Gly Lys Ser Asn Gly Glu Lys Lys Tyr
            -80              -75                  -70

ATT GTC GGG TTT AAA CAG ACA ATG AGC ACG ATG AGC GCC GCT AAG AAG         617
Ile Val Gly Phe Lys Gln Thr Met Ser Thr Met Ser Ala Ala Lys Lys
            -65              -60                  -55

AAA GAT GTC ATT TCT GAA AAA GGC GGG AAA GTG CAA AAG CAA TTC AAA         665
Lys Asp Val Ile Ser Glu Lys Gly Gly Lys Val Gln Lys Gln Phe Lys
            -50              -45                  -40

TAT GTA GAC GCA GCT TCA GCT ACA TTA AAC GAA AAA GCT GTA AAA GAA         713
Tyr Val Asp Ala Ala Ser Ala Thr Leu Asn Glu Lys Ala Val Lys Glu
-35             -30                  -25                  -20

TTG AAA AAA GAC CCG AGC GTC GCT TAC GTT GAA GAA GAT CAC GTA GCA         761
Leu Lys Lys Asp Pro Ser Val Ala Tyr Val Glu Glu Asp His Val Ala
            -15              -10                   -5

CAT GCG TAC GCG CAG TCC GTG CCT TAC GGC GTA TCA CAA ATT AAA GCC         809
His Ala Tyr Ala Gln Ser Val Pro Tyr Gly Val Ser Gln Ile Lys Ala
         1               5                   10

CCT GCT CTG CAC TCT CAA GGC TAC ACT GGA TCA AAT GTT AAA GTA GCG         857
Pro Ala Leu His Ser Gln Gly Tyr Thr Gly Ser Asn Val Lys Val Ala
         15              20                  25

GTT ATC GAC AGC GGT ATC GAT TCT TCT CAT CCT GAT TTA AAG GTA GCA         905
Val Ile Asp Ser Gly Ile Asp Ser Ser His Pro Asp Leu Lys Val Ala
30              35                  40                  45

GGC GGA GCC AGC ATG GTT CCT TCT GAA ACA AAT CCT TTC CAA GAC AAC         953
Gly Gly Ala Ser Met Val Pro Ser Glu Thr Asn Pro Phe Gln Asp Asn
                50                  55                  60

AAC TCT CAC GGA ACT CAC GTT GCC GGC ACA GTT GCG GCT CTT AAT AAC        1001
Asn Ser His Gly Thr His Val Ala Gly Thr Val Ala Ala Leu Asn Asn
            65                  70                  75

TCA ATC GGT GTA TTA GGC GTT GCG CCA AGC GCA TCA CTT TAC GCT GTA        1049
Ser Ile Gly Val Leu Gly Val Ala Pro Ser Ala Ser Leu Tyr Ala Val
            80                  85                  90

AAA GTT CTC GGT GCT GAC GGT TCC GGC CAA TAC AGC TGG ATC ATT AAC        1097
Lys Val Leu Gly Ala Asp Gly Ser Gly Gln Tyr Ser Trp Ile Ile Asn
    95                  100                 105

GGA ATC GAG TGG GCG ATC GCA AAC AAT ATG GAC GTT ATT AAC ATG AGC        1145
Gly Ile Glu Trp Ala Ile Ala Asn Asn Met Asp Val Ile Asn Met Ser
110                 115                 120                 125

CTC GGC GGA CCT TCT GGT TCT GCT GCT TTA AAA GCG GCA GTT GAT AAA        1193
Leu Gly Gly Pro Ser Gly Ser Ala Ala Leu Lys Ala Ala Val Asp Lys
                130                 135                 140

GCC GTT GCA TCC GGC GTC GTA GTC GTT GCG GCA GCC GGT AAC GAA GGC        1241
Ala Val Ala Ser Gly Val Val Val Val Ala Ala Ala Gly Asn Glu Gly
            145                 150                 155

ACT TCC GGC AGC TCA AGC ACA GTG GGC TAC CCT GGT AAA TAC CCT TCT        1289
Thr Ser Gly Ser Ser Ser Thr Val Gly Tyr Pro Gly Lys Tyr Pro Ser
        160                 165                 170

GTC ATT GCA GTA GGC GCT GTT GAC AGC AGC AAC CAA AGA GCA TCT TTC        1337
Val Ile Ala Val Gly Ala Val Asp Ser Ser Asn Gln Arg Ala Ser Phe
    175                 180                 185
```

| | | | | | | | | | | | | | | | | |
|---|---|---|---|---|---|---|---|---|---|---|---|---|---|---|---|---|
| TCA | AGC | GTA | GGA | CCT | GAG | CTT | GAT | GTC | ATG | GCA | CCT | GGC | GTA | TCT | ATC | 1385 |
| Ser | Ser | Val | Gly | Pro | Glu | Leu | Asp | Val | Met | Ala | Pro | Gly | Val | Ser | Ile | |
| 190 | | | | 195 | | | | | | 200 | | | | | 205 | |
| CAA | AGC | ACG | CTT | CCT | GGA | AAC | AAA | TAC | GGG | GCG | TAC | AAC | GGT | ACG | TCA | 1433 |
| Gln | Ser | Thr | Leu | Pro | Gly | Asn | Lys | Tyr | Gly | Ala | Tyr | Asn | Gly | Thr | Ser | |
| | | | | 210 | | | | | 215 | | | | | 220 | | |
| ATG | GCA | TCT | CCG | CAC | GTT | GCC | GGA | GCG | GCT | GCT | TTG | ATT | CTT | TCT | AAG | 1481 |
| Met | Ala | Ser | Pro | His | Val | Ala | Gly | Ala | Ala | Ala | Leu | Ile | Leu | Ser | Lys | |
| | | | 225 | | | | | 230 | | | | | 235 | | | |
| CAC | CCG | AAC | TGG | ACA | AAC | ACT | CAA | GTC | CGC | AGC | AGT | TTA | GAA | AAC | ACC | 1529 |
| His | Pro | Asn | Trp | Thr | Asn | Thr | Gln | Val | Arg | Ser | Ser | Leu | Glu | Asn | Thr | |
| | | 240 | | | | | 245 | | | | | 250 | | | | |
| ACT | ACA | AAA | CTT | GGT | GAT | TCT | TTC | TAC | TAT | GGA | AAA | GGG | CTG | ATC | AAC | 1577 |
| Thr | Thr | Lys | Leu | Gly | Asp | Ser | Phe | Tyr | Tyr | Gly | Lys | Gly | Leu | Ile | Asn | |
| | 255 | | | | | 260 | | | | | 265 | | | | | |
| GTA | CAG | GCG | GCA | GCT | CAG | TAA | A | ACATAAAAAA | | CCGGCTTGG | | CCCCGCCGGT | | | | 1629 |
| Val | Gln | Ala | Ala | Ala | Gln | * | | | | | | | | | | |
| 270 | | | | | 275 | | | | | | | | | | | |
| TTTTTATTAT | TTTTCTTCCT | CCGCATGTTC | AATCCGCTCC | ATAATCGACG | GATGGCTCCC | 1689 |
| TCTGAAAATT | TTAACGAGAA | ACGGCGGGTT | GACCCGGCTC | AGTCCCGTAA | CGGCCAAGTC | 1749 |
| CTGAAACGTC | TCAATCGCCG | CTTCCCGGTT | TCCGGTCAGC | TCAATGCCGT | AACGGTCGGC | 1809 |
| GGCGTTTTCC | TGATACCGGG | AGACGGCATT | CGTAATCGGA | TCAGAAGCAA | AACTGAGCA | 1868 |

CALCIUM FREE SUBTILISIN MUTANTS

This application is a divisional of application Ser. No. 08/069,863, filed Jun. 1, 1993, and issued as U.S. Pat. No. 5,470,733 on Nov. 28, 1995.

STATEMENT REGARDING FEDERALLY SPONSORED RESEARCH

The U.S. Government has a paid-up license in this invention and the right in limited circumstances to require the patent owner to license others on reasonable terms as provided for by the terms of Grant No. GM42560 awarded by National Institute of Health.

GENERAL OBJECTS OF THE INVENTION

A general object of the invention is to provide subtilisin mutants which have been mutated such that they do not bind calcium.

Another object of the invention is to provide DNA sequences which upon expression provide for subtilisin mutants which do not bind calcium.

Another object of the invention is to provide subtilisin mutants which comprise specific combinations of mutations which provide for enhanced thermal stability.

Another object of the invention is to provide a method for the synthesis of a subtilisin mutant which does not bind calcium by the expression of a subtilisin DNA which comprises one or more substitution, deletion or addition mutations in a suitable recombinant host cell.

A more specific object of the invention is to provide subtilisin BPN' mutants which have been mutated such that they do not bind calcium.

Another specific object of the invention is to provide DNA sequences which upon expression result in subtilisin BPN' mutants which do not bind calcium.

Another specific object of the invention is to provide a method for making subtilisin BPN' mutants which do not bind calcium by expression of a subtilisin BPN' DNA coding sequence which comprises one or more substitution, addition or deletion mutations in a suitable recombinant host cell.

Yet another specific object of the invention is to provide subtilisin BPN' mutants which do not bind calcium and which further comprise particular combinations of mutations which provide for enhanced thermal stability, or which restore cooperativity to the folding reaction.

The subtilisin mutants of the present invention are to be utilized in applications where subtilisins find current usage. Given that these mutants do not bind calcium they should be particularly well suited for use in industrial environments which comprise chelating agents, e.g. detergent compositions, which substantially reduces the activity of wild-type type calcium binding subtilisins.

BACKGROUND OF THE INVENTION

(1) Field of the Invention

The present invention relates to subtilisin proteins which have been modified to eliminate calcium binding. More particularly, the present invention relates to novel subtilisin BPN' mutants wherein amino acids 75–83 have been deleted, and which may additionally comprise other mutations which provide for enhanced thermal stability or mutations which restore cooperativity to the folding reaction.

(2) Description of the Related Art

Subtilisin is an unusual example of a monomeric protein with a substantial kinetic barrier to folding and unfolding. For example, subtilisin BPN' is a 275 amino acid serine protease secreted by *Bacillus amyloliquefaciens*. It is an enzyme of considerable industrial importance and has been the subject of numerous protein engineering studies (Siezen et al., *Protein Engineering* 4:719–737 (1991); Bryan, *Pharmaceutical Biotechnology* 3(B):147–181 (1992); Wells et al., *Trends Biochem. Sci.* 13:291–297 (1988)). The amino acid sequence for subtilisin BPN' may be found in Vasantha et al., *J. Bacteriol.* 159:811–819 (1984), and the amino acid sequence as found therein is hereby incorporated by reference. Throughout the application, when Applicants refer to the amino acid sequence of subtilisin BPN' or its mutants, they are referring to the amino acid sequence as listed therein.

Subtilisin is a serine protease produced by Gram positive bacteria or by fungi. The amino acid sequences of numerous subtilisins are known. (Siezen et al., *Protein Engineering* 4:719–737 (1991)). These include five subtilisins from Bacillus strains, for example, subtilisin BPN', subtilisin Carlsberg, subtilisin DY, subtilisin amylosacchariticus, and mesenticopoptidase. (Vasantha et al., "Gene for alkaline protease and neutral protease from *Bacillus amyloliquefaciens* contain a large open-reading frame between the regions coding for signal sequence and mature protein," *J. Bacteriol.* 159:811–819 (1984); Jacobs et al., "Cloning sequencing and expression of subtilisin Carlsberg from *Bacillus licheniformis*," *Nucleic Acids Res.* 13:8913–8926 (1985); Nedkov et al., "Determination of the complete amino acid sequence of subtilisin DY and its comparison with the primary structures of the subtilisin BPN', Carlsberg and amylosacchariticus," *Biol. Chem. Hoppe-Seyler* 366:421–430 (1985); Kurihara et al., "Subtilisin amylosacchariticus," *J. Biol. Chem.* 247:5619–5631 (1972); and Svendsen et al., "Complete amino acid sequence of alkaline mesentericopeptidase," *FEBS Lett.* 183:195–200 (1985)).

The amino acid sequences of subtilisins from two fungal proteases are known: proteinase K from *Tritirachium albam* (Jany et al., "Proteinase K from Tritirachium albam Limber," *Biol. Chem. Hoppe-Seyler* 366:485–492 (1985)) and thermomycolase from the thermophilic fungus, *Malbranchea pulchella* (Gaucher et al., "Endopeptidases: Thermomycolin," *Methods Enzymol.* 45:415–433 (1976)).

These enzymes have been shown to be related to subtilisin BPN', not only through their primary sequences and enzymological properties, but also by comparison of x-ray crysallographic data. (McPhalen et al., "Crystal and molecular structure of the inhibitor eglin from leeches in complex with subtilisin Carlsberg," *FEBS Lett.*, 188:55–58 (1985) and Pahler et al., "Three-dimensional structure of fungal proteinase K reveals similarity to bacterial subtilisin," *EMBO J.*, 3:1311–1314 (1984)).

Subtilisin BPN' is an example of a particular subtilisin gene secreted by *Bacillus amyloliquefaciens*. This gene has been cloned, sequenced and expressed at high levels from its natural promoter sequences in *Bacillus subtilis*. The subtilisin BPN' structure has been highly refined (R=0.14) to 1.3 Å resolution and has revealed structural details for two ion binding sites (Finzel et al., *J. Cell. Biochem. Suppl.* 10A:272 (1986); Pantoliano et al., *Biochemistry* 27:8311–8317 (1988); McPhalen et al., *Biochemistry* 27: 6582–6598 (1988)). One of these (site A) binds $Ca^{2+}$ with high affinity and is located near the N-terminus, while the other (site B)

binds calcium and other cations much more weakly and is located about 32 Å away (FIG. 1). Structural evidence for two calcium binding sites was also reported by Bode et al., *Eur. J. Biochem.* 166:673–692 (1987) for the homologous enzyme, subtilisin Carlsberg.

Calcium binding sites are common features of extracellular microbial proteases probably because of their large contribution to both thermodynamic and kinetic stability (Matthews et al., *J. Biol. Chem.* 249:8030–8044 (1974); Voordouw et al., *Biochemistry* 15:3716–3724 (1976); Betzel et al., *Protein Engineering* 3:161–172 (1990); Gros et al., *J. Biol. Chem.* 266:2953–2961 (1991)). The thermodynamic and kinetic stability of subtilisin is believed to be necessitated by the rigors of the extracellular environment into which subtilisin is secreted, which by virtue of its own presence is protease-filled. Accordingly, high activation barriers to unfolding may be essential to lock the native conformation and prevent transient unfolding and proteolysis.

Unfortunately, the major industrial uses of subtilisins are in environments containing high concentrations of metal chelators, which strip calcium from subtilisin and compromise its stability. It would, therefore, be of great practical significance to create a highly stable subtilisin which is independent of calcium.

The present inventors have previously used several strategies to increase the stability of subtilisin to thermal denaturation by assuming simple thermodynamic models to approximate the unfolding transition (Pantoliano et al., *Biochemistry* 26:2077–2082 (1987); Pantoliano et al., *Biochemistry* 27:8311–8317 (1988); Pantoliano et al., *Biochemistry* 28:7205–7213 (1989); Rollence et al., *CRC Crit. Rev. Biotechnol.* 8:217–224 (1988). However, improved subtilisin mutants which are stable in industrial environments, e.g., which comprise metal chelators and which do not bind calcium, are currently not available.

OBJECTS AND SUMMARY OF THE INVENTION

Accordingly, it is an object of the invention to provide mutated or modified subtilisin enzymes which have been modified to eliminate calcium binding. As used in this invention, the term "mutated or modified subtilisin" is meant to include any serine protease enzyme which has been modified to eliminate calcium binding. This includes, in particular, subtilisin BPN' and serine proteases which are homologous to subtilisin BPN'. However, as used herein, and under the definition of mutated or modified subtilisin enzyme, the mutations of this invention may be introduced into any serine protease which has at least 50%, and preferably 80% amino acid sequence homology with the sequences referenced above for subtilisin BPN', subtilisin Carlsberg, subtilisin DY, subtilisin amylosacchariticus, mesenticopeptidase, thermitase, proteinase K, or thermomycolase, and, therefore, may be considered homologous.

The mutated subtilisin enzymes of this invention are more stable in the presence of metal chelators and may also comprise enhanced thermal stability in comparison to native or wild-type subtilisin. Thermal stability is a good indicator of the overall robustness of a protein. Proteins of high thermal stability often are stable in the presence of chaotropic agents, detergents, and under other conditions, which normally tend to inactivate proteins. Thermally stable proteins are, therefore, expected to be useful for many industrial and therapeutic applications in which resistance to high temperature, harsh solvent conditions or extended shelf-life is required.

It has been further discovered that combining individual stabilizing mutations in subtilisin frequently results in approximately additive increases in the free energy of stabilization. Thermodynamic stability has also been shown to be related to resistance to irreversible inactivation at high temperature and high pH. The single-site changes of this invention individually do not exceed a 1.5 Kcal/mol contribution to the free energy of folding. However, these small incremental increases in the free energy of stabilization result in dramatic increases in overall stability when mutations are combined, since the total free energy of folding for most proteins is in the range of 5–15 Kcals/mol (Creighton, *Proteins: Structure and Molecular Properties*, W. H. Freeman and Company, New York (1984)).

X-ray crystallographic analysis of several combination mutants reveals that conformational changes associated with each mutation tend to be highly localized with minimal distortion of the backbone structure. Thus, very large increases in stability can be achieved with no radical changes in the tertiary protein structure and only minor independent alterations in the amino acid sequence. As previously suggested (Holmes et al, *J. Mol. Biol.* 160:623 (1982)), contributions to the free energy of stabilization can be gained in different ways, including improved hydrogen bonding and hydrophobic interactions in the folded form and decreased chain entropy of the unfolded enzyme.

This is significant since thermostable enzymes generally have more extended half-lives at broader temperature ranges, thereby improving bio-reactor and shelf-life performance.

As noted supra, the invention provides subtilisin mutants which comprise one or more deletion, substitution or addition mutations which provide for the elimination of calcium binding. In the case of subtilisin BPN', the subtilisin mutants will preferably comprise one or more addition, deletion or substitution mutations of the amino acids at positions 75–83, and most preferably will comprise the deletion of amino acids 75–83. The deletion of amino acids 75–83 has been discovered to effectively eliminate calcium binding to the resultant subtilisin mutant while still providing for subtilisin BPN' proteins having enzymatic activity.

Such subtilisin mutants lacking amino acids 75–83 may further include one or more additional amino acid mutations in the sequence, e.g., mutations which provide for reduced proteolysis. It is another object of the invention to produce subtilisin mutants lacking calcium binding activity which have been further mutated to restore cooperativity to the folding reaction and thereby enhance proteolytic stability. It is another object of the invention to provide thermostable subtilisin mutants which further do not bind calcium and comprise specific combinations of mutations which provide for substantially enhanced thermal stability.

In particular, the subtilisin mutants of the present invention will include subtilisins from Bacillus strains, such as subtilisin BPN', subtilisin Carlsberg, subtilisin DY, subtilisin amylosacchariticus and subtilisin mesenticopeptidase, which comprise one or more deletion, substitution or addition mutations.

BRIEF DESCRIPTION OF THE DRAWINGS

FIG. 1. X-ray Crystal structure of S15 subtilisin

A. α-carbon plot shows the positions of mutations as noted. The numbering of wild type subtilisin is kept. Dotted spheres show the position of calcium at the weak ion binding site (B-site) and the former position of the high affinity binding site (A-site). The A-site loop (dashed line) is absent in this mutant. N- and C- termini are indicated. The N-terminus is disordered (dotted line).

B. Close-up view of the A-site deletion. The loop from S12 subtilisin is shown as a dotted line with the continuous helix of S15. Superimposed is the 3* sigma difference electron density (FO12-FO15, phases from S15) showing the deleted A-site loop.

FIG. 3. Differential Scanning Calorimetry. The calorimetric scans of apo-S12 ($T_m$=63.5° C.) and S15 ($T_m$=63.0° C.) are shown. Measurements were performed with a Hart 7707 DSC (differential scanning calorimetry) heat conduction scanning microcalorimeter as described (Pantoliano et al., Biochemistry 28:7205–7213 (1989)). Sample conditions were 50 mM of glycine, a pH of 9.63, a scan rate of 0.5° C./min. Excess heat capacity is measured in units of μJ/°. The calorimeter ampoules contained 1.78 mg of protein.

FIG. 4. Titration calorimetry of subtilisin S11. The heat of calcium binding for successive additions of calcium are plotted vs. the ratio of [Ca]/[P]. The data are best fit by a calculated binding curve assuming a binding constant of $7 \times 10^6$ and ΔH equal to 11.3 kcal/mol using equation (1) from the text. For comparison, calculated curves assuming $K_a$=$1 \times 10^6$ and $1 \times 10^8$ are also shown. In this titration, [P]=100 μM and the temperature was 25° C.

FIG. 5. Kinetics of calcium dissociation from subtilisin S11 as a function of temperature. 1 μM subtilisin S11 was added to 10 μM Quin2 at time=0. Calcium dissociates from subtilisin and binds to Quin2 until a new equilibrium is achieved. The rate of calcium dissociation is followed by the increase in fluorescence of Quin2 when it binds to calcium.

A. The log of the percent of the protein bound to calcium is plotted vs. time. The kinetics of dissociation at four temperatures are shown. The dissociation follows first order kinetics for the first 25% of the reaction. As this is well before equilibrium is approached, reassociation of calcium can be neglected.

B. Temperature dependence of the rate of calcium dissociation from S15 subtilisin in the presence of excess Quin2, pH 7.4 and over a temperature range of 25°–45° C. The natural log of the equilibrium constant for the transition state (calculated from the Eyring equation) is plotted vs. the reciprocal of the absolute temperature. The line is fit according to equation (3) in the text with $T_0$=298 K.

DESCRIPTION OF THE PREFERRED EMBODIMENTS

As discussed supra, calcium binding contributes substantially to the thermo-dynamic and kinetic-stability of extracellular microbial proteases. Moreover, with respect to subtilisin, high activation barriers to unfolding may be essential to retain the native conformation and to prevent transient unfolding and proteolysis given the protease-filled environment where subtilisin is secreted and as a result of auto-degradation. The unfolding reaction of subtilisin can be divided into two parts as follows:

where N(Ca) is the native form of subtilisin with calcium bound to the high affinity calcium-binding site A (Finzel et al., J. Cell. Biochem. Suppl. 10A:272 (1986); Pantoliano et al., Biochemistry, 27:8311–8317 (1988); McPhalen et al., Biochemistry 27:6582–6598 (1988)); N is the folded protein without calcium bound; and U is the unfolded protein. Subtilisin is a relatively stable protein whose stability is in large part mediated by the high affinity calcium site (Voordrouw et al., Biochemistry 15:3716–3724 (1976); Pantoliano et al., Biochemistry 27:8311–8317 (1988)). The melting temperature of subtilisin at pH 8.0 in the presence of μmolar concentrations of calcium is approximately 75° C. and approximately 56° C. in the presence of excess EDTA (Takehashi et al., Biochemistry 20:6185–6190 (1981); Bryan et al., Proc. Natl. Acad. Sci. USA, 83:3743–3745 (1986b)). Previous calorimetric studies of the calcium-free (apoenzyme, i.e., protein portion of enzyme) form of subtilisin indicated that it is of marginal stability at 25° C. with a ΔG of unfolding of <5 kcal/mol (Pantoliano et al., Biochemistry 28:7205–7213 (1989)). Because calcium is such an integral part of the subtilisin structure, the apoenzyme is thought to be a folding intermediate of subtilisin.

In order to independently examine the two phases of the folding process, the present inventors constructed a series of mutant subtilisins. First, all proteolytic activity was eliminated in order to prevent auto-degradation from occurring during the unfolding and refolding reactions. This may be accomplished, for example, by converting the active-site serine 221 to cysteine.[1] This mutation has little effect on the thermal denaturation temperature of subtilisin, but reduces peptidase activity of subtilisin by a factor of approximately $3 \times 10^4$ (Abrahmsen et al., Biochemistry 30:4151–4159 (1991)). This mutant, therefore, allows the folding of subtilisin to be studied without the complications of proteolysis. In the present specification, a shorthand for denoting amino acid substitutions employs the single letter amino acid code of the amino acid to be substituted, followed by the number designating where in the amino acid sequence the substitution will be made, and followed by the single letter code of the amino acid to be inserted therein. For example, S221C denotes the substitution of serine 221 to cysteine. The subtilisin mutant with this single amino acid substitution is denoted subtilisin S221C. The resulting S221C subtilisin mutant is designated S1.

[1] The S221A mutant was originally constructed for this purpose. The mature form of this mutant was heterogeneous on its N-terminus, however, presumably due to some incorrect processing of the pro-enzyme.

The subtilisin may be further mutated in order to make the relatively unstable apoenzyme easier to produce and purify. Versions of S1 with three or four additional mutations, for example, M50F, Q206I, Y217K and N218S, may also be employed in the method of the present invention. Such further mutations cumulatively increase the free energy of unfolding by 3.0 kcal/mol and increase the thermal denaturation temperature of the apoenzyme by 11.5° C. (Pantoliano et al., Biochemistry 28:7205–7213 (1989)). The mutant containing the M50F, Q206I, Y217K, N218S and S221C mutations is designated S11 and the mutant containing the M50F, Y217K, N218S and S221C is designated S12.[2]

[2] The specific activities of S11, S12 and S15 against the synthetic substrate, SAAPFna, are the same. (S.A.=0.0024 U/mg at 25° C., pH 8.0). These measurements were performed on protein freshly purified on a mercury affinity column.

Figure 1A:
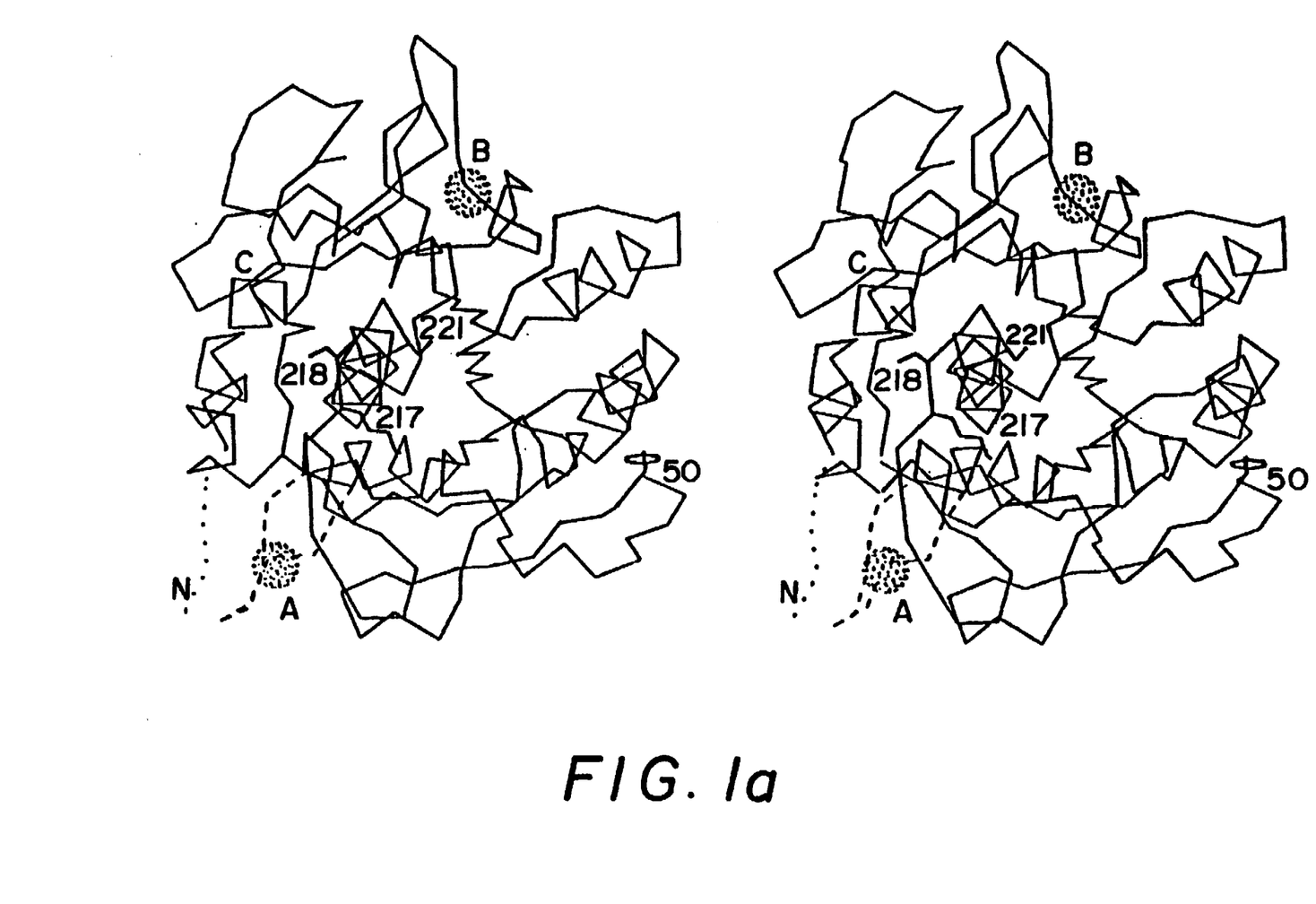
Figure 1B:
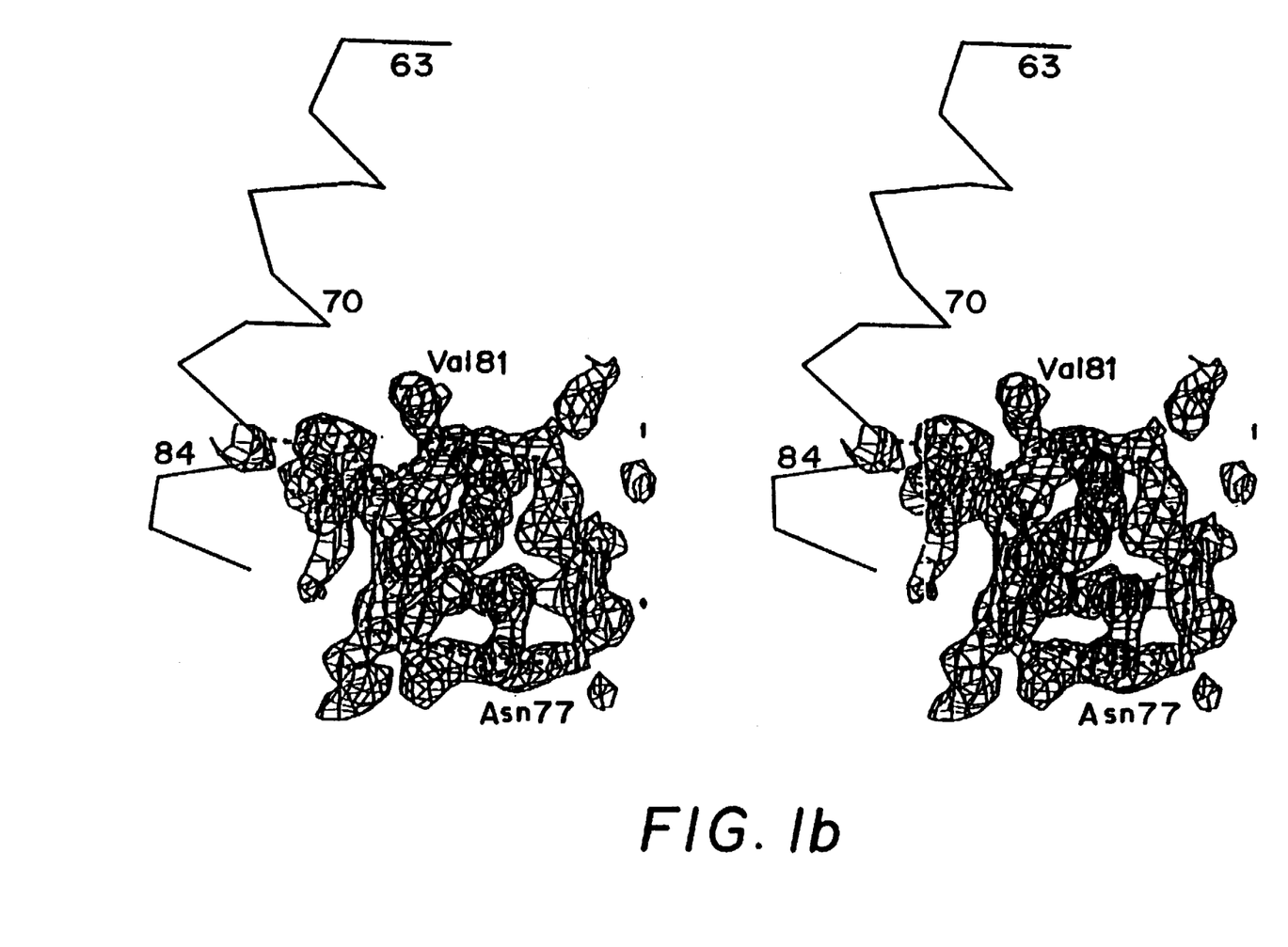

In order to produce a subtilisin BPN' protein lacking calcium binding activity, the present inventors elected to delete the binding loop in the calcium A-site to engineer a novel calcium-free subtilisin protein. This loop comprises an interruption in the subtilisin BPN' α-helix involving amino acids 63–85 (McPhalen and James 1988). Residues 75–83 of the subtilisin BPN' protein form a loop which interrupts the last turn of the 14-residue alpha helix involving amino acids 63–85. Four of the six ligands to the calcium are provided by this loop. Therefore, site-directed mutagenesis was used to delete amino acids 75–83, which creates an uninterrupted helix and abolishes the calcium binding potential at site A (FIG. 1A and 1B).

While the present inventors chose to eliminate calcium binding by the removal of these amino acids, it should be possible to eliminate calcium binding by other mutations, e.g., substitution of one or more of the amino acids at positions 75–83 with alternative amino acids. This may also be accomplished by site-specific mutagenesis.

In particular, the present inventors synthesized by site-specific mutagenesis three subtilisin BPN' DNA's which have been mutated to eliminate amino acids 75–83 involved in calcium binding and which further comprise additional substitution mutations. These mutated subtilisin BPN' DNA's, upon expression of the DNA, provide for subtilisin proteins having enhanced thermal stability or which prevent proteolysis.

The specific subtilisin BPN' mutants synthesized by the present inventors are designated in this application as S15, S39 and S47. The S15 mutant comprises a deletion of amino acids 75–83 and additionally comprises the following substitution mutations: S221C, N218S, M50F and Y217K. The S39 mutant similarly comprises a deletion of amino acids 75–83 and additionally comprises the following substitution mutations: S221C, P5A, N218S, M50F and Y217K. The third mutant, S47, comprises a deletion of amino acids 75–83 and additionally comprises the following substitution mutations: P5A, N218S, M50F and Y217K. The specific activity of the proteolytically active S47 subtilisin has been found to be very similar to the wild-type enzyme. The various Δ75–83 subtilisins which were synthesized by the inventors are shown in Table 1 below. The synthesis of these mutants is described in more detail infra.

TABLE 1

| | Subtilisin Mutations | | | | | | |
|---|---|---|---|---|---|---|---|
| | S221C | P5A | Δ75–83 | N218S | M50F | Q206I | Y217k |
| BPN' | – | – | – | – | – | – | – |
| S1* | + | – | – | – | – | – | – |
| S11* | + | – | – | + | + | + | + |
| S12* | + | – | – | + | + | – | + |
| S15* | + | – | + | + | + | – | + |
| S39 | + | + | + | + | + | – | + |
| S47 | – | + | + | + | + | – | + |

The plus signs show that a subtilisin contains a particular mutation. X-ray crystal structures of wild type, S12 and S15 have been determined to 1.8Å, *S1, S11, S12, S15 and S39 are low activity mutants constructed to aid in the evaluation of structure and conformational stability.

In order to understand the contribution of calcium binding to the stability of subtilisin, the thermodynamics and kinetics of calcium binding to the high affinity calcium A-site were measured by microcalorimetry and fluorescence spectroscopy. Calcium binding is an enthalpically driven process with an association constant ($K_a$) equal to $7 \times 10^6 M^{-1}$. The kinetic barrier to calcium removal from the A-site (23 kcal/mol) is substantially larger than the standard free energy of binding (9.3 kcal/mol). The kinetics of calcium dissociation from subtilisin (e.g., in excess EDTA) are accordingly very slow. For example, the half-life ($t_{1/2}$) of calcium dissociation from subtilisin, i.e., the time for half of the calcium to dissociate from subtilisin, is 1.3 hours at 25° C.

X-ray crystallography shows that except for the region of the deleted calcium-binding loop, the structure of the S47 mutant and wild type protein are very similar. The N-terminus of the wild-type protein lies beside the site A loop and furnishes one calcium coordination ligand, the side chain oxygen of Q2. In Δ75–83 subtilisin, the loop is gone, leaving residues 1–4 disordered. However, as previously noted the helix is uninterrupted and shows normal helical geometry over its entire length. X-ray crystallography further shows that the structures of subtilisin with and without the deletion superimpose with a root mean square (r.m.s.) difference between 261 α-carbon positions of 0.17 Å, and are remarkably similar considering the size of the deletion. Diffuse difference density and higher temperature factors, however, indicate some disorder in the newly exposed residues adjacent to the deletion.

While the elimination of calcium binding is advantageous since it produces proteins that are more stable in the presence of metal chelators, it is disadvantageous in at least one respect. Specifically, the elimination of the calcium loop without any other compensating mutations results in the destabilization of the native state relative to the partially folded states and, therefore, a loss of cooperativity in folding. The present inventors thus sought to further genetically engineer the subtilisin S15 BPN' protein lacking amino acids 75–83 in order to restore cooperativity to the folding reaction. In most well designed proteins all parts of the molecule are interdependent, making the unfolding reaction highly cooperative. Cooperativity of the folding reaction allows proteins to achieve sufficient stabilities of the native state for proper function since the overall stability of the native conformation is roughly the sum of all local interactions.

Therefore, while the Δ75–83 subtilisin is an example of an engineered subtilisin which is active and stable in the absence of calcium, the present inventors sought to improve this protein by further mutation. The design of a particular highly stable calcium-free subtilisin relies on an iterative engineering cycle. The present inventors found that the requisite first step in the cycle was to greatly diminish the proteolytic activity of subtilisin. This is necessary because calcium contributes greatly to the conformational stability of subtilisin and the early versions of calcium-free subtilisin are susceptible to proteolysis. After reducing the susceptibility to proteolysis, the next step in the cycle was to eliminate sequences essential for calcium binding, i.e., the A-site. Although the S15 Δ75–83 subtilisin is much less stable than the wild type subtilisin in the presence of calcium, this mutant is more stable than wild type subtilisin in the presence of the metal chelator EDTA.

Accordingly, the third step was to improve the stability of the calcium-free subtilisin protein. To improve the stability of calcium-free subtilisin, the present inventors next tried to create a home for the disordered N-terminal residues. In order to create a highly stable calcium-free subtilisin, the N-terminal part of the protein which is destabilized by the deletion of the calcium A-loop may be modified. For example, the N-terminus which is disordered may be deleted or extended. This, however, is problematic because the requirements for processing the propeptide from the mature protein are not known. It is known, however, that the processing site is not determined by amino acid sequence since mutants Y1A (the C-terminus of the propeptide), A1C and Q2R do not alter the site of cleavage. It is also known that the native structure of the N-terminus in subtilisin does not determine the cleavage site because the Δ75–83 variants are processed correctly. Since it is not yet known how to alter the processing site, interactions with the existing N-terminus may be optimized.

The first attempt was to mutate the proline at position 5 to alanine to create more flexibility at position 5. This increased flexibility allows the N-terminus to try to find a unique position along the new surface of the protein, created by deletion of the calcium loop. Once the N-terminus assumes a unique location its local interactions may then be optimized.

The P5A mutation was made to try to create more flexibility for the N-terminus and allow it to find a unique position along the new surface of the protein that was created by deletion of the calcium loop. In the native structure, the first five amino acids are in an extended conformation and form β-pair hydrogen bonds with the calcium loop as well as the Q2 side chain interaction with the calcium. The proline at position 5, which is conserved among seven bacterial subtilisins which have a homologous calcium A-site, may help stabilize the extended conformation. The P5A mutation in Δ75–83 subtilisin should thus result in an increase in the cooperativity of the unfolding reaction. The X-ray structure of this variant has been determined to 1.8 Å.

In addition to the N-terminus, there are three other residues whose side chain conformations are distinctly different from wild type in Δ75–83 subtilisin. Y6 swings out of a surface niche into a more solvent-exposed position, as an indirect effect of the destabilization of the N-terminus. D41, a former calcium ligand, and Y214 undergo a coordinated rearrangement, forming a new hydrogen bond. The B-factors of all three residues increase significantly due to the deletion. In addition, S87 and A88 do not change conformation but exhibit significantly increased B-factors. Proline 86 terminates the α-helix from which the calcium loop was deleted. Therefore, other mutants comprising mutations at one or more of these sites or the amino acids proximate thereto may provide for subtilisin BPN' mutants comprising greater enzymatic activity or increased stability.

In order to identify mutants of increased stability any technique known by those skilled in the art may be used. One example of such a technique for generating and screening subtilisin variants involves three steps: 1) in vitro mutagenesis of the cloned subtilisin gene; 2) expression of mutated genes in *B. subtilis*, and 3) screening for enhanced stability. The key element in the random mutagenesis approach is being able to screen large numbers of variants. To accomplish this, the present inventors devised a method to bind the subtilisin secreted from individual colonies to nitrocellulose filters and then assay the filter bound activity. To screen for thermostable variants, filters containing bound subtilisin are incubated at temperatures high enough to rapidly inactivate nearly all parental hydrolytic activity. Variants of increased stability will have higher activity after the heating step. Once a preliminary identification of a stable variant is made from the nitrocellulose filter, the corresponding colony is isolated and the variant subtilisin further characterized.

Although random mutagenesis may be employed, the mutagenesis procedure described above allows for mutations to be directed to localized regions of the protein (e.g., the N-terminal region). As noted supra, the S47 mutant (which comprise the active-site S221) was found to be enzymatically active. It is expected that other substitutions should provide for even greater stability and activity.

Thus, the present inventors have provided convincing evidence that subtilisin mutants may be obtained which remain active and yet do not bind calcium, and which may therefore be utilized in industrial environments that comprise chelating agents. While this has only been specifically shown with subtilisin BPN', the subject mutants should work with other serine proteases as well.

Such strategies, for example, may involve comparing the sequence of subtilisin BPN' to other serine proteases in order to identify the amino acids which are suspected to be necessary for calcium binding and then making suitable modifications, e.g., by site-specific mutagenesis. Since many subtilisins are related to subtilisin BPN' not only through their primary sequences and enzymological properties, but also by X-ray crystallographic data, it is expected that other active subtilisin mutants which lack calcium binding may be produced by site specific mutagenesis. For example, structural evidence exists that the homologous enzyme subtilisin Carlsberg also comprises two calcium binding sites. Accordingly, this enzyme should also be amenable to mutations which eliminate these calcium binding sites.

Alternatively, if the amino acids which comprise the calcium binding sites are already known for a particular subtilisin, the corresponding DNA will be mutated by site specific mutagenesis to delete one or more of such amino acids, or to provide substitution, deletion or addition mutations which eliminate calcium binding.

The subject mutant subtilisins will generally be produced by recombinant methods, in particular by expression of a subtilisin DNA which has been mutated such that upon expression it results in a subtilisin protein which is enzymatically active and which does not bind calcium.

Preferably, the subtilisin DNA's will be expressed in microbial host cells, in particular *Bacillus subtilis* since this bacteria naturally produces subtilisin, is an efficient secretor of proteins, and is able to produce the protein in an active conformation. However, the invention is not restricted to the expression of the subtilisin mutant in Bacillus, but rather embraces expression in any host cell which provides for expression of the desired subtilisin mutants. Suitable host cells for expression are well known in the art and include, e.g., bacterial host cells such as *Escherichia coli*, Bacillus, Salmonella, Pseudomonus; yeast cells such as *Saccharomyces cerevisiae, Pichia pastoris*, Kluveromyces, Candida, Schizosaccharomyces; and mammalian host cells such as CHO cells. Bacterial host cells, of course, are the preferred host cells for expression.

Expression of the subtilisin DNA will be provided using available vectors and regulatory sequences. The actual selection will depend in large part upon the particular host cells used for expression. For example, if the subtilisin mutant DNA is expressed in Bacillus, a Bacillus promoter will generally be utilized as well as a Bacillus derived vector. The present inventors in particular used the pUB110-based expression vector and used the native promoter from the subtilisin BPN' gene to control expression on *Bacillus subtilis*.

It is further noted that once the amino acid sequence of a particular subtilisin mutant which does not bind calcium has been elucidated, it may also be possible to make the subtilisin mutant by protein synthesis, e.g., by Merrifield synthesis. However, expression of the subtilisin mutants in microbial host cells will generally be preferred since this will allow for the microbial host cell to produce the subtilisin protein in a proper conformation for enzymatic activity. However, since the present inventors further teach herein a method for obtaining in vitro refolding of the subtilisin mutant, it should be possible to convert improperly folded subtilisin mutants into an active conformation.

In order to further illustrate the present invention and the advantages thereof, the following specific examples are given, it being understood that the same is intended only as illustrative and in nowise limitative.

EXAMPLES

Example 1

Cloning and Expression The subtilis in gene from *Bacillus amyloliquefaciens* (subtilisin BPN') has been cloned, sequenced, and expressed at high levels from its natural promoter sequences in *Bacillus subtilis* (Wells et al., *Nucleic Acids Res.* 11:7911–7925 (1983); Vasantha et al., *J. Bacteriol.* 159:811–819 (1984)). All mutant genes were recloned into a pUB110-based expression plasmid and used to transform *B. subtilis*. The *B. subtilis* strain used as the host contains a chromosomal deletion of its subtilisin gene and therefore produces no background wild type (wt) activity (Fahnestock et al., *Appl. Environ. Microbial.* 53:379–384 (1987)). Oligonucleotide mutagenesis was carried out as previously described. (Zoller et al., *Methods Enzymol.* 100:468–500 (1983); Bryan et al., *Proc. Natl. Acad. Sci.* 83:3743–3745 (1986b)). S221C was expressed in a 1.51 New Brunswick fermentor at a level of approximately 100 mg of the correctly processed mature form per liter. The addition of wild type subtilisin to promote production of the mature form of S221C subtilisin was not required in our bacillus host strain as was the case for prior swains (Abrahmsen et al., *Biochemistry* 30:4151–4159 (1991)).

Protein Purification & Characterization. Wild type subtilisin and the variant enzymes were purified and verified for homogeneity essentially as described in Bryan et al., *Proc. Natl. Acad. Sci.* 83:3743–3745 (1986b); Pantoliano et al., *Biochemistry* 26:2077–2082 (1987); and *Biochemistry* 27:8311–8317 (1988). In some cases the C221 mutant subtilisins were re-purified on a sulfhydryl specific mercury affinity column (Affi-gel 501, Biorad). Assays of peptidase activity were performed by monitoring the hydrolysis of succinyl-(L)-Ala-(L)-Ala-(L)-Pro-(L)-Phe-p-nitroanilide, hereinafter sAAPFna, as described by DelMar et al., *Anal Biochem.* 99:316–320 (1979). The protein concentration, [P], was determined using $P^{0.1\%}=1.17$ at 280 nm (Pantoliano et al, *Biochemistry* 28:7205–7213 (1989)). For variants which contain the Y217K change, the $P^{0.1\%}$ at 280 nm was calculated to be 1.15 (or 0.96×wt), based on the loss of one Tyr residue (Pantoliano et al., *Biochemistry* 28:7205–7213 (1989)).

N-Terminal Analysis The first five amino acids of subtilisin S15 were determined by sequential Edman degradation and HPLC analysis. This revealed that 100% of the material had the amino acid sequence expected from the DNA sequence of the gene and that processing of the pro-peptide was at the same position in the sequence for the mutant as for the wild type enzyme.

Example 2

Figure 2:
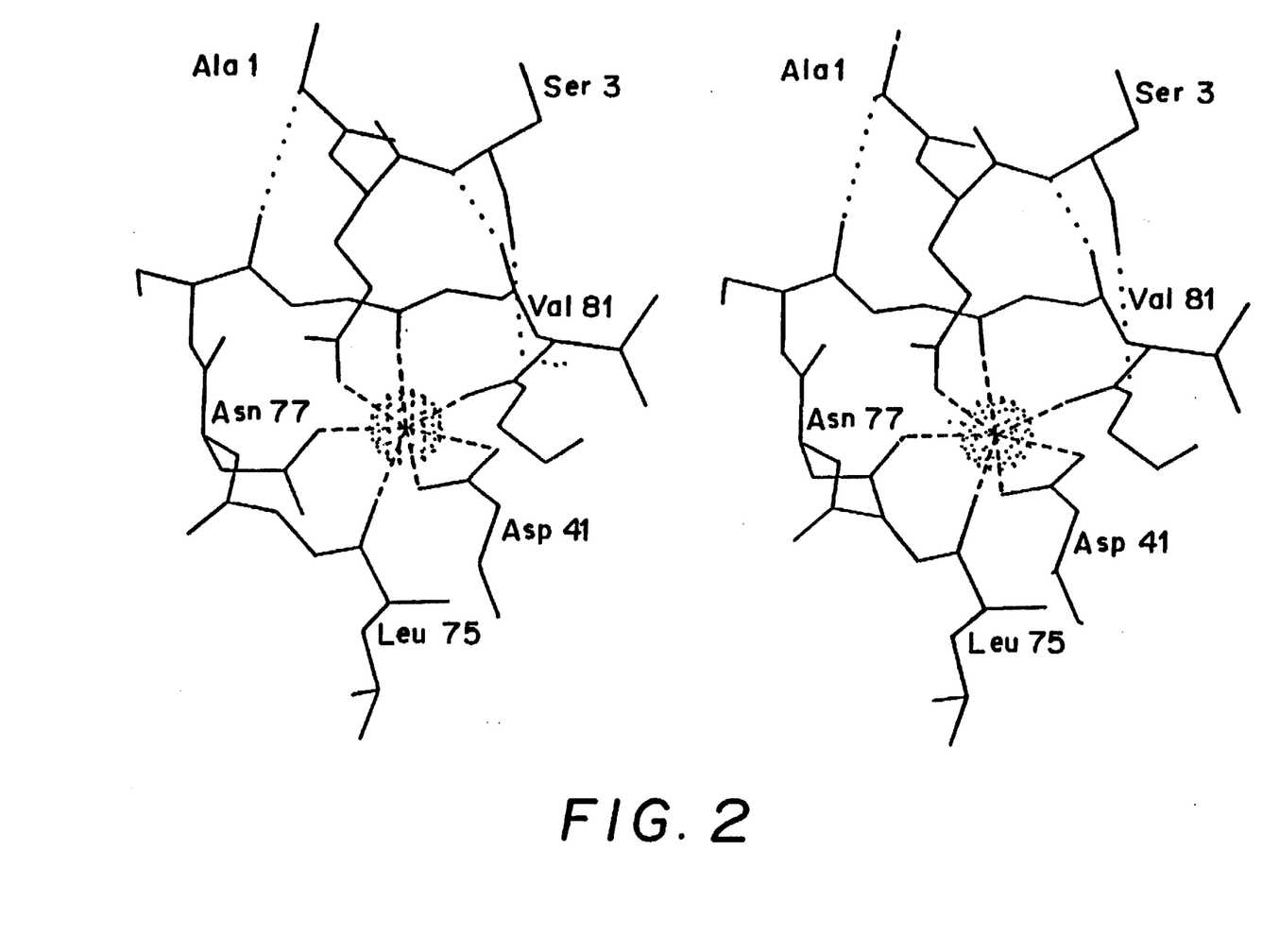
FIG. 2. X-ray crystal structure of the calcium A-site region of S12 subtilisin. Calcium is shown as a dotted sphere with one-half the van der Waals radius. Dashed lines are coordination bonds, while dotted lines represent hydrogen bonds under 3.2 Å.

Structure of the calcium A site of S12 subtilisin Calcium at site A is coordinated by five carbonyl oxygen ligands and one aspartic acid. Four of the carbonyl oxygen ligands to the calcium are provided by a loop composed of amino acids 75–83 (FIG. 2). The geometry of the ligands is that of a pentagonal bipyramid whose axis runs through the carbonyls of 75 and 79. On one side of the loop is the bidentate carboxylate (D41), while on the other side is the N-terminus of the protein and the side chain of Q2. The seven coordination distances range from 2.3 to 2.6 Å, the shortest being to the aspartyl carboxylate. Three hydrogen bonds link the N-terminal segment to loop residues 78–82 in parallel-beta arrangement.

Preparation of apo-subtilisin S11 and S12 subtilisin contain an equal molar amount of tightly bound calcium after purification. X-ray crystallography has shown this calcium to be bound to the A site (Finzel et al., *J. Cell. Biochem. Suppl.* 10A:272 (1986); Pantoliano et al., *Biochemistry* 27:8311–8317 (1988); McPhalen et al., *Biochemistry* 27:6582–6598 (1988)).

Complete removal of calcium from subtilisin is very slow, requiring 24 hours of dialysis against EDTA at 25° C. to remove all calcium from the protein and then 48 more hours of dialysis in high salt (Brown et al., *Biochemistry* 16:3883–3896 (1977)) at 4° C. to remove all EDTA from the protein. To prepare the calcium-free form of subtilisins S11 and S12, 20 mg of lyophilized protein was dissolved in 5 ml of 10 mM, EDTA, 10 mM tris(hydroxymethyl)aminomethane hydrochloric acid (hereinafter Tris-HCl) at pH 7.5 and dialyzed against the same buffer for 24 hours at 25° C. In order to remove EDTA, which binds to subtilisin at low ionic strength, the protein was then dialyzed twice against 2 liters of 0.9M NaCl, 10 mM Tris-HCl at pH 7.5 at 4° C. for a total of 24 hours and then three times against 2 liters of 2.5 mM Tris-HCl at pH 7.5 at 4° C. for a total of 24 hours. Chelex 100 was added to all buffers not containing EDTA. When versions of C221 subtilisin not containing stabilizing amino acid substitutions were used, up to 50% of the protein precipitated during this procedure. It is essential to use pure native apoenzyme in titration experiments so that spurious heat produced by precipitation upon the addition of calcium does not interfere with the measurement of the heat of binding.

To ensure that preparations of apo-subtilisin were not contaminated with calcium or EDTA, samples were checked by titration with calcium in the presence of Quin2 prior to performing titration calorimetry.

Titration Calorimetry Measurements The calorimetric titrations were performed with a Microcal Omega titration calorimeter as described in detail by Wiseman et al., *Analytical Biochemistry* 179:131–137 (1989). The titration calorimeter consists of a matched reference cell containing the buffer and a solution cell (1.374 mL) containing the protein solution. Microliter aliquots of the ligand solution are added to the solution cell through a rotating stirrer syringe operated with a plunger driven by a stepping motor. After a stable baseline was achieved at a given temperature, the automated injections were initiated and the accompanying heat change per injection was determined by a thermocouple sensor between the cells. During each injection, a sharp exothermic peak appeared which returned to the baseline prior to the next injection occurring 4 minutes later. The area of each peak represents the amount of heat accompanying binding of the added ligand to the protein. The total heat (Q) was then fit by a nonlinear least squares minimization method (Wiseman et al., *Analytical Biochemistry* 179:131–137 (1989)) to the total ligand concentration, $[Ca]_{total}$, according to the equation:

$$dQ/d[Ca]_{total} = \Delta H[\frac{1}{2} + (1-(1+r)/2 - X_r/2)/X_r - 2X_r(1-r) + 1 + r^2)^{\frac{1}{2}}] \quad (1)$$

wherein $1/r = [P]_{total} \times K_a$ and $X_r = [Ca]_{total}/[P]_{total}$.

The binding of calcium to the S11 and S12 subtilisins was measured by titration calorimetry as it allows both the binding constant and the enthalpy of binding to be determined (Wiseman et al., *Analytical Biochemistry* 179:131–137 (1989); Schwarz et al., *J. Biol. Chem.* 266:24344–24350 (1991)).

Figure 4:
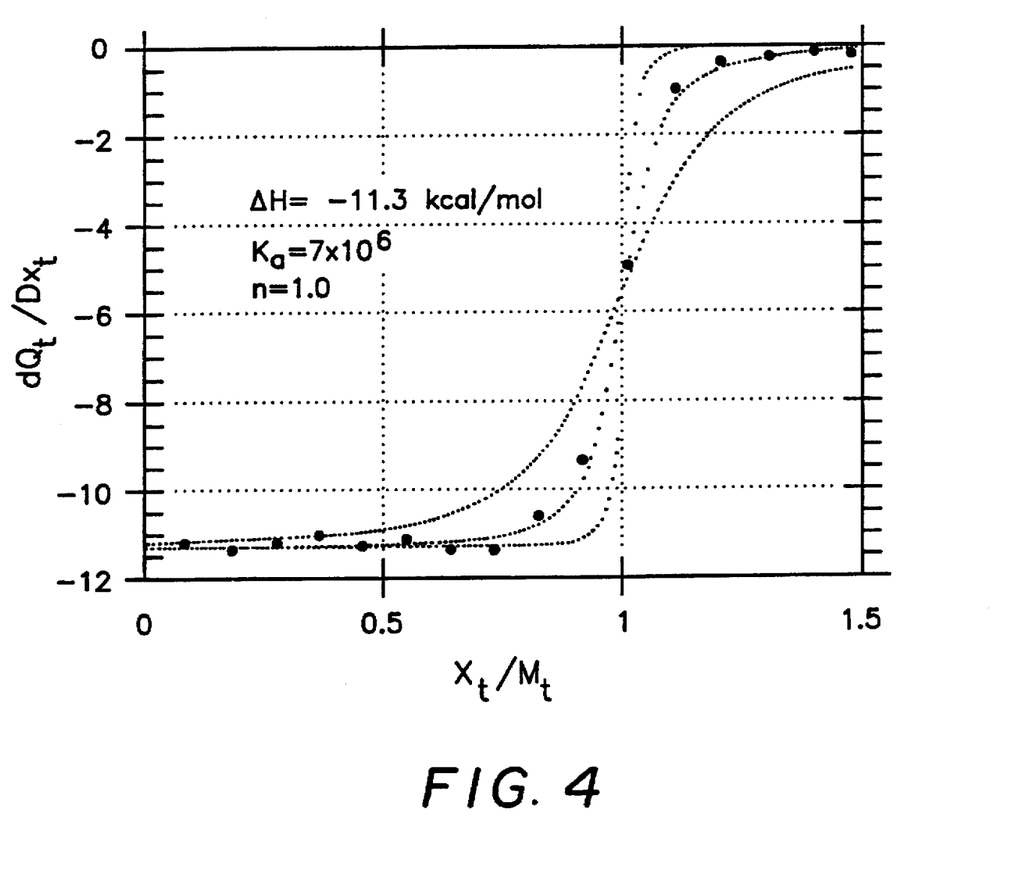

The S11 and S12 subtilisin mutants were used in titration experiments because production of the wild type apoenzyme is impossible due to its proteolytic activity and low stability. Titrations of S11 and S12 were performed at protein concentrations [P]=30 µM and 100 µM. Titration of the S11 apoenzyme with calcium at 25° C. is shown in FIG. 4. The data points correspond to the negative heat of calcium binding associated with each titration of calcium. The titration calorimeter is sensitive to changes in $K_a$ under conditions at which the product of $K_a \times [P]$ is between 1 and 1000 (Wiseman et al., *Analytical Biochemistry* 179:131–137 (1989)). Since the $K_a$ for subtilisin is about $1 \times 10^7 M^{-1}$, these protein concentrations result in values of $K_a \times [P] = 300$ and 1000. At lower protein concentrations the amount of heat produced per titration is difficult to measure accurately.

The results of fitting the titrations of S11 and S12 to a calculated curve are summarized in Table 2. The parameters in the table include binding parameters for stoichiometric ratio (n), binding constant ($K_a$) and binding enthalpy ($\Delta H$). These parameters were determined from deconvolution using nonlinear least squares minimization (Wiseman et al., *Analytical Biochemistry* 179:131–137 (1989)). Measurements for each experimental condition were performed in duplicate at 25° C. The protein concentrations ranged from 30 to 100 μM while the concentration of the calcium solutions were about 20 times the protein concentrations. Each binding constant and enthalpy were based on several titration runs at different concentrations. Titration runs were performed until the titration peaks were close to the baseline.

TABLE 2

Titration Calorimetry of the Calcium A Site in Subtilisin Mutants S11 and S12.

| | | Parameters calculated from fit | | |
|---|---|---|---|---|
| Mutant | [P] | n | $K_a$ | $\Delta H$ |
| S11 | 100 μM | 0.98 ± 0.01 | 7.8 ± 0.2 × 10$^6$ | −11.3 ± 0.1 |
| S11 | 33 μM | 0.9 ± 0.3 | 6.8 ± 1.5 × 10$^6$ | −10.9 ± 0.2 |
| S12 | 100 μM | 0.99 ± 0.01 | 6.4 ± 0.2 × 10$^6$ | −11.8 ± 0.5 |

The average values obtained are similar for S11 and S12: $\Delta H = -11$ kcal/mol; $K_a = 7 \times 10^6 M^{-1}$ and a stoichiometry of binding of 1 calcium site per molecule. The weak binding site B does not bind calcium at concentrations below the millimolar range, and therefore does not interfere with measurement of binding to the binding site A. The standard free energy of binding at 25° C. is 9.3 kcal/mol. The binding of calcium is therefore primarily enthalpically driven with only a small net loss in entropy ($\Delta S_{binding} = -6.7$ cal/°mol).

Example 3

In vitro refolding of S15 subtilisin. For refolding studies subtilisin was maintained as a stock solution in 2.5 mM Tris-HCl at pH 7.5 and 50 mM KCl at a concentration of approximately 100 μM. The protein was denatured by diluting the stock solution into 5M guanidine hydrochloride (Gu-HCl) at pH 7.5 or in most cases into 25 mM $H_3PO_4$ or HCl at pH 1.8–2.0. The final concentration of protein was 0.1 to 5 μM. S15 was completely denatured in less than 30 seconds by these conditions. S12 required approximately 60 minutes to become fully denatured. Acid-denatured protein was then neutralized to pH 7.5 by the addition of Tris-base (if denatured in HCl) or 5M NaOH (if denatured in $H_3PO_4$). Refolding was initiated by the addition of KCl, NaCl or $CaCl_2$ to the desired concentration. For example, KCl was added from a stock solution of 4M to a final concentration of 0.1 to 1.5M with rapid stirring. In most cases renaturation was carried out at 25° C. The rate of renaturation was determined spectrophotometrically by uv absorption from the increase in extinction at $\lambda = 286$, from the increase in intrinsic tyrosine and tryptophan fluorescence (excitation $\lambda = 282$, emission $\lambda - 347$), or by circular dichroism from the increase in negative ellipticity at $\lambda = 222$ nm.

Example 4

X-ray Crystallography. Large single crystal growth and X-ray diffraction data collection were performed essentially as previously reported (Bryan et al., *Proteins: Struct. Funct. Genet.* 1:326–334 (1986a); Pantoliano et al., *Biochemistry.* 27:8311–8317 (1988); Pantoliano et al., *Biochemistry* 28:7205–7213 (1989)) except that it was not necessary to inactivate the S221C variants with diisopropyl fluorophosphate (DFP) in order to obtain suitable crystals. The starting model for S12 was made from the hyperstable subtilisin mutant 8350 (Protein Data Bank entry 1SO1.pdb). The S12 structure was refined and then modified to provide the starting model for S15.

Data sets with about 20,000 reflections between 8.0 Å and 1.8 Å resolution were used to refine both models using restrained least-squares techniques (Hendrickson et al., "Computing in Crystallography" in Diamond et al., eds., *Bangalore: Indian Institute of Science* 13.01–13.23 (1980)). Initial difference maps for S15, phased by a version of S12 with the entire site A region omitted, clearly showed continuous density representing the uninterrupted helix, permitting an initial S15 model to be constructed and refinement begun. Each mutant was refined from R approximately 0.30 to R approximately 0.18 in about eighty cycles, interspersed with calculations of electron density maps and manual adjustments using the graphics modeling program FRODO (Jones, *J. Appl. Crystallogr.* 11:268–272 (1978)).

Except for the region of the deleted calcium-binding loop, the structures of S12 and S15 are very similar, with a root mean square (r.m.s) deviation of 0.18 Å between 262 α-carbons. The N-terminus of S12 (as in the wild-type) lies beside the site A loop, furnishing one calcium coordination ligand, the side chain oxygen of Q2. In S15 the loop is gone, leaving residues 1–4 disordered. In S12 (as in wild type) the site A loop occurs as an interruption in the last turn of a 14-residue alpha helix; in S15 this helix is uninterrupted and shows normal helical geometry over its entire length. Diffuse difference density and higher temperature factors indicate some disorder in the newly exposed residues adjacent to the deletion.

Example 5

Figure 3:
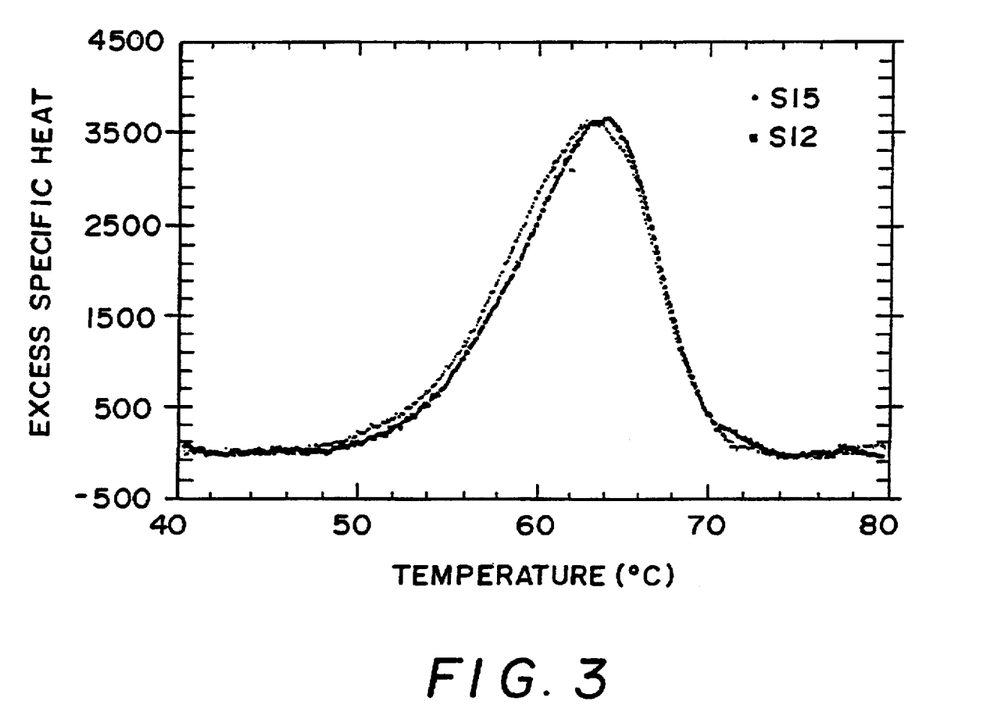

Differential Scanning Calorimetry The stability properties of S12 and S15 were studied using DSC (differential scanning calorimetry). The Δ75–83 mutant (S15) is very similar in melting temperature to the apoenzyme of S12. The DSC profiles of apo-S12 and S15 are shown in FIG. 3. The temperature of maximum heat capacity is 63.0° C. for S15 and 63.5° C. for apo-S12 at pH 9.63. The DSC experiments were carried out at high pH to avoid aggregation during the denaturation process. The amount of excess heat absorbed by a protein sample as the temperature increased through a transition from the folded to unfolded state at constant pressure, which provided a direct measurement of the ΔH of unfolding (Privalov et al., *Methods Enzymol.* 131:4–51 (1986)). $\Delta H_{cal}$ of unfolding for apo-S12 and S15 is about 140 kcal/mol. Above pH 10.0, the unfolding transition for S15 fit a two-state model reasonably well, consistent with equilibrium thermodynamics as expressed in the van't Hoff equation (dln K/dT=$\Delta H_{vH}/(RT^2)$) with $\Delta H_{vH}$ (the van't Hoff enthalpy or apparent enthalpy) approximately equal to $\Delta H_{cal}$ (the calorimetric or true enthalpy). At pH 9.63, however, the melting profile for both proteins was asymmetric indicating that the unfolding is not a pure two-state process.

Example 6

Measuring kinetics of calcium dissociation. The dissociation of calcium from subtilisin is a slow process. To measure this rate the fluorescent calcium chelator Quin 2 was used.

Figure 5A:
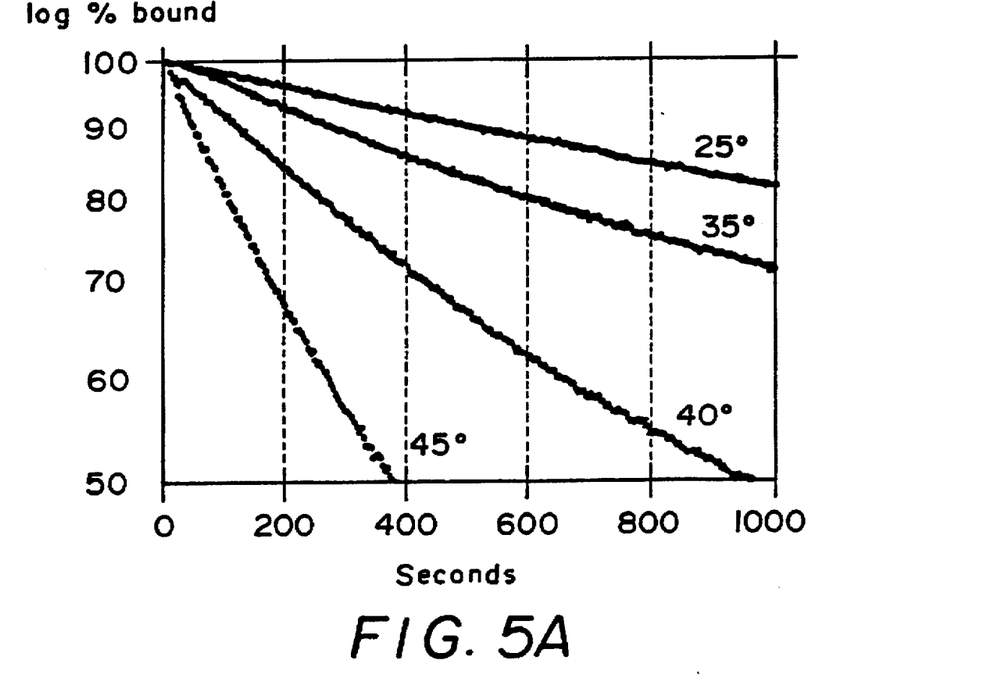

Quin 2 binds calcium with a $K_a$ of $1.8 \times 10^8$ at pH 7.5 (Linse et al., *Biochemistry* 26:6723–6735 (1987)). The fluorescence of Quin 2 at 495 nm increases by approximately 6-fold when bound to calcium (Bryant, *Biochem. J.* 226:613–616 (1985)). Subtilisin S11 or S12 as isolated contains one calcium ion per molecule. When mixed with an excess of Quin 2, the kinetics of calcium release from the protein can be followed from the increase in fluorescence at 495 nm. The reaction is assumed to follow the pathway N(Ca)→N+Ca+Quin 2 →Quin(Ca). The dissociation of calcium from subtilisin is very slow relative to calcium binding by Quin 2, such that the change in fluorescence of Quin 2 is equal to the rate of calcium dissociation from subtilisin. As can be seen in FIG. 5a, the initial release of calcium from S11 follows simple first order kinetics.

Figure 5B:
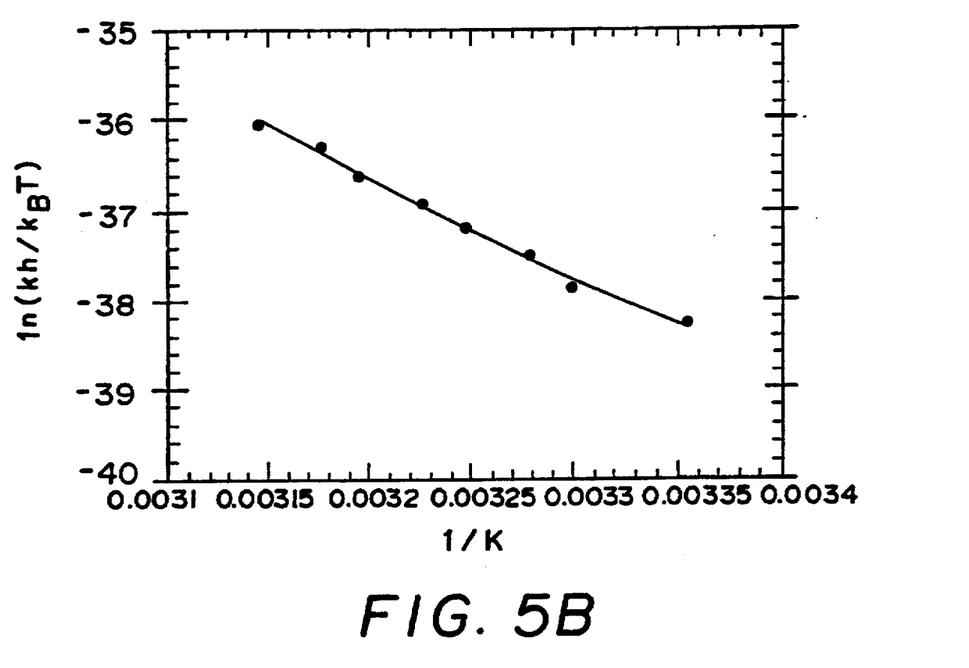

Temperature dependence of calcium dissociation The first order rate constant (k) for calcium dissociation was measured from 20° to 45° C. The plot of ln k vs. $1/T°$ K. is roughly linear. The calcium dissociation data was curve fit using transition state theory according to the Erying equation:

$$\Delta G^{\ddagger} = -RT \ln K^{\ddagger} = -RT \ln kh/k_B T \quad (2)$$

wherein $k_B$ is the Boltzman constant, h is Planck's constant and k is the first order rate constant for folding. A graph of ln $hk/k_B T$ vs. $1/T$ is shown in FIG. 5b.

The data was then curve fit according to the equation (Chen et al., *Biochemistry* 28:691–699 (1989)):

$$\ln K^{\ddagger} = A + B(T_o/T) + C \ln (T_o/T) \quad (3)$$

wherein $A=[\Delta Cp^{\ddagger} + \Delta S^{\ddagger}(T_o)]/R$; $B=A-\Delta G^{\ddagger}(T_o)/RT_o$; $C=\Delta Cp^{\ddagger}/R$. The data obtained yields the following results: $\Delta G^{\ddagger}=22.7$ kcal/mol; $\Delta Cp^{\ddagger}=-0.2$ kcal/°mol; $\Delta S^{\ddagger}=-10$ cal/°mol; and $\Delta H^{\ddagger}=19.7$ kcal/mol at a reference temperature of 25° C. A possible slight curvature of the plot would be due to a change in heat capacity associated with formation of the transition state ($\Delta Cp^{\ddagger}=0.2$ kcal/°mol). $\Delta Cp$ for protein folding has been shown to be closely correlated with a change in exposure of hydrophobic groups to water (Privalov et al., *Adv. Protein Chem.* 39:191–234 (1988); Livingstone et al., *Bochemistry* 30:4237–4244 (1991)). In terms of heat capacity, the transition state therefore appears similar to the native protein. The values for $\Delta S'^{\ddagger}$ and $\Delta H'^{\ddagger}$ obtained from FIG. 5b indicate that the transition state is enthalpically less favorable than the calcium bound form with only a small change in entropy.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

All references cited herein are incorporated in their entirety, as if individually incorporated by reference.

What is claimed is:

1. A DNA comprising a nucleic acid sequence encoding a mutated subtilisin protein which has been modified to lack the ability to bind calcium at a high affinity calcium binding site, wherein said encoded subtilisin mutant comprises a deletion of amino acids corresponding to the amino acids at positions 75–83 of mature subtilisin BPN'.

2. The DNA of claim 1, wherein the nucleic acid sequence encoding said mutant subtilisin comprises a deletion of nucleotides corresponding to the nucleotides at positions 993–1019 of SEQ ID NO:1.

3. The DNA of claim 1 further comprising a transcriptional promoter and other regulatory DNA sequence elements suitable for expression of the encoded mutant subtilisin in a transformed host cell.

4. The DNA of claim 3, wherein said encoded subtilisin mutant is selected from the group consisting of a subtilisin BPN' mutant, a subtilisin Carlsberg mutant, a subtilisin DY mutant, a subtilisin amylosacchariticus mutant, and a subtilisin mesentericopeptidase mutant.

5. The DNA of claim 1 further comprising one or more substitution mutations which provide for enhanced thermal stability or which provide for the restoration of cooperativity of folding of the subtilisin mutant protein.

6. The DNA of claim 5 which, upon expression, results in a subtilisin BPN' mutant selected from the group consisting of S15, S39 and S47.

7. The DNA of claim 6 which, upon expression, results in the mutant subtilisin BPN' mutant S47.

8. An expression vector comprising the DNA of claim 1.
9. An expression vector comprising the DNA of claim 2.
10. An expression vector comprising the DNA of claim 3.
11. An expression vector comprising the DNA of claim 4.
12. An expression vector comprising the DNA of claim 5.
13. An expression vector comprising the DNA of claim 6.
14. An expression vector comprising the DNA of claim 7.
15. A transformed host cell comprising the DNA of claim 1.
16. A transformed host cell comprising the DNA of claim 2.
17. A transformed host cell comprising the DNA of claim 3.
18. A transformed host cell comprising the DNA of claim 4.
19. A transformed host cell comprising the DNA of claim 5.
20. A transformed host cell comprising the DNA of claim 6.
21. A transformed host cell comprising the DNA of claim 7.
22. A recombinant method for the production of a subtilisin mutant which lacks the ability to bind calcium at a high affinity calcium binding site comprising:
   (a) transforming microbial host cells with an expression vector comprising the DNA of claim 1 which permits the expression of a subtilisin mutant lacking the ability to bind calcium at a high affinity calcium binding site;
   (b) culturing said host cells under conditions which provide for the expression of said subtilisin mutant; and,
   (c) recovering the expressed subtilisin mutant from said microbial host cells.

23. The method of claim 22, wherein said subtilisin mutant is selected from the group consisting of a subtilisin BPN' mutant, a subtilisin Carlsberg mutant, a subtilisin DY mutant, a subtilisin amylosacchariticus mutant, and a subtilisin mesentericopeptidase mutant.

24. The method of claim 23, wherein said subtilisin mutant is the subtilisin BPN' mutant.

25. The method of claim 24, wherein said subtilisin BPN' mutant DNA comprises one or more additional mutations which provide for enhanced thermal stability or which provide for the restoration of cooperativity of folding of the subtilisin mutant protein.

26. The method of claim 25, wherein said subtilisin mutant is selected from S15, S39 and S47.

27. The method of claim 26, wherein said subtilisin mutant is S47.

* * * * *